US 7,727,235 B2

(12) United States Patent  (10) Patent No.: US 7,727,235 B2
Contiliano et al.  (45) Date of Patent: Jun. 1, 2010

(54) MEDICAL FIXATION DEVICES WITH IMPROVED TORSIONAL DRIVE HEAD

(75) Inventors: Joseph H. Contiliano, Somerville, NJ (US); Yufu Li, Bridgewater, NJ (US); Zhigang Li, Hillsborough, NJ (US)

(73) Assignee: Ethicon, Inc., Norwood, MA (US)

( * ) Notice: Subject to any disclaimer, the term of this patent is extended or adjusted under 35 U.S.C. 154(b) by 434 days.

(21) Appl. No.: 11/170,377

(22) Filed: Jun. 29, 2005

(65) Prior Publication Data

US 2007/0010820 A1    Jan. 11, 2007

(51) Int. Cl.
  *A61F 5/00*    (2006.01)
(52) U.S. Cl. .................... 606/86 A; 606/319; 606/104; 411/410; 81/52; 81/121.1
(58) Field of Classification Search ............ 606/72–73, 606/76–77, 104, 300, 305–308, 319, 321, 606/86 A; 411/394, 398–399, 402–404, 411/407–408, 410, 426, 405, 419; 81/121.1, 81/124.2, 52, 437, 124.1; 72/454; 279/148, 279/155
See application file for complete search history.

(56) References Cited

U.S. PATENT DOCUMENTS

| | | | | | |
|---|---|---|---|---|---|
| 94,601 | A | * | 9/1869 | Heywood | 411/402 |
| 374,701 | A | * | 12/1887 | Quinby | 411/402 |
| 671,789 | A | * | 4/1901 | Borgeson | 81/124.1 |
| 975,285 | A | * | 11/1910 | Robertson | 411/403 |
| 1,380,562 | A | * | 6/1921 | Keating | 81/460 |
| 1,432,243 | A | * | 10/1922 | Harris | 411/133 |
| 1,434,401 | A | * | 11/1922 | Mueller | 81/124.2 |
| 1,715,975 | A | * | 6/1929 | Angell | 411/81 |
| 1,946,800 | A | * | 2/1934 | MacLean | 411/399 |
| 2,016,610 | A | * | 10/1935 | Moeller | 411/424 |
| 2,248,695 | A | * | 7/1941 | Bradshaw | 411/410 |
| 2,811,883 | A | * | 11/1957 | Cleaves | 81/124.1 |
| 2,836,095 | A | * | 5/1958 | Devine | 411/385 |
| 3,065,662 | A | * | 11/1962 | Spoehr et. al. | 411/399 |
| 3,086,414 | A | * | 4/1963 | Nardi | 81/176.1 |
| 3,157,942 | A | * | 11/1964 | MacLean, Jr. | 29/432 |

(Continued)

FOREIGN PATENT DOCUMENTS

EP    068 637 A1    12/1995

(Continued)

OTHER PUBLICATIONS

PCT International Search Report for PCT/US2006/025737 Jul. 11, 2006.

*Primary Examiner*—Thomas C Barrett
*Assistant Examiner*—James L. Swiger
(74) *Attorney, Agent, or Firm*—Nutter McClennen & Fish LLP (57) ABSTRACT

The present invention provides a fixation device that includes an elongate shank defining a longitudinal axis and having at least one engaging member for applying the fixation device within tissue and securing the fixation device in the tissue once implanted formed thereon, and a drive head having a proximal end, a distal end and a radial cross-sectional geometry, where the drive head is mated to the elongate shank, and includes at least one anti-rotational member integral therewith. Fixation device kits utilizing the fixation device, and methods of fixation in tissue are also provided.

18 Claims, 6 Drawing Sheets

U.S. PATENT DOCUMENTS

| | | | | |
|---|---|---|---|---|
| D203,412 S | * | 1/1966 | Wing | D8/387 |
| D203,947 S | * | 3/1966 | Pick | D8/387 |
| 3,466,748 A | * | 9/1969 | Christensen | 433/189 |
| D248,014 S | * | 5/1978 | DeCaro | D8/387 |
| D274,881 S | * | 7/1984 | Wilsey | D8/29 |
| 4,459,074 A | * | 7/1984 | Capuano | 411/403 |
| 4,616,535 A | * | 10/1986 | Chiavon | 81/121.1 |
| 4,938,731 A | * | 7/1990 | Nguyen et al. | 464/158 |
| 4,976,715 A | * | 12/1990 | Bays et al. | 606/77 |
| 5,017,079 A | * | 5/1991 | Reynolds | 411/432 |
| 5,059,077 A | * | 10/1991 | Schmid | 411/400 |
| 5,129,906 A | * | 7/1992 | Ross et al. | 606/77 |
| 5,207,679 A | * | 5/1993 | Li | 606/232 |
| 5,249,899 A | * | 10/1993 | Wilson | 411/82 |
| 5,324,308 A | * | 6/1994 | Pierce | 606/232 |
| 5,364,400 A | * | 11/1994 | Rego et al. | 606/72 |
| 5,370,662 A | * | 12/1994 | Stone et al. | 606/232 |
| 5,378,101 A | * | 1/1995 | Olson et al. | 411/405 |
| D355,343 S | * | 2/1995 | Gliddings, Jr. | D8/82 |
| 5,443,482 A | | 8/1995 | Stone et al. | |
| 5,516,248 A | * | 5/1996 | DeHaitre | 411/387.2 |
| 5,573,548 A | | 11/1996 | Nazre et al. | |
| 5,736,152 A | | 4/1998 | Dunn | |
| 5,824,011 A | | 10/1998 | Stone et al. | |
| 5,837,752 A | | 11/1998 | Shastri et al. | |
| 5,868,789 A | | 2/1999 | Huebner | |
| 5,990,194 A | | 11/1999 | Dunn et al. | |
| 6,045,554 A | | 4/2000 | Grooms et al. | |
| 6,045,573 A | * | 4/2000 | Wenstrom et al. | 606/232 |
| 6,139,565 A | | 10/2000 | Stone et al. | |
| 6,159,008 A | * | 12/2000 | Kumar | 433/163 |
| 6,269,716 B1 | * | 8/2001 | Amis | 81/121.1 |
| 6,343,531 B2 | | 2/2002 | Amis | |
| 6,368,322 B1 | | 4/2002 | Luks et al. | |
| 6,486,232 B1 | | 11/2002 | Wise et al. | |
| 6,679,668 B2 | * | 1/2004 | Martin et al. | 411/388 |
| 6,743,233 B1 | * | 6/2004 | Baldwin et al. | 606/73 |
| 7,338,491 B2 | * | 3/2008 | Baker et al. | 606/308 |
| 2002/0017170 A1 | | 2/2002 | Amis | |
| 2002/0052605 A1 | | 5/2002 | Grooms et al. | |
| 2002/0173822 A1 | * | 11/2002 | Justin et al. | 606/232 |
| 2003/0083662 A1 | | 5/2003 | Middleton | |
| 2003/0120280 A1 | * | 6/2003 | Roller et al. | 606/77 |
| 2004/0082956 A1 | | 4/2004 | Baldwin et al. | |
| 2004/0254580 A1 | | 12/2004 | Boock et al. | |
| 2005/0043735 A1 | | 2/2005 | Ahmad | |
| 2005/0090828 A1 | | 4/2005 | Alford | |

FOREIGN PATENT DOCUMENTS

| | | |
|---|---|---|
| EP | 0791331 A | 8/1997 |
| EP | 1486171 A | 12/2004 |

\* cited by examiner

MEDICAL FIXATION DEVICES WITH IMPROVED TORSIONAL DRIVE HEAD

FIELD OF THE INVENTION

The present invention relates to medical fixation devices having improved physical properties, more particularly, to biologically compatible fixation devices requiring torsional forces to secure their application within body tissue.

BACKGROUND OF THE INVENTION

Within the medical field, fixation devices are used in different ways to assist in the reconstruction of damaged body tissue. A fixation device may be used to directly secure tissue in close approximation to neighboring tissue to effect healing such as is the case with meniscal fixation devices, or fracture fixation pins, screws, or wires. Other types of fixation devices are intended to provide mechanical stability and load sharing during the healing process, as when a graft is secured in a bone tunnel for ACL reconstruction. Fixation devices may also be used in conjunction with other device hardware such as plates, rods, or various other connecting members known in the art as part of an implant assembly, such as with a spinal screw fixing a plate to the vertebral body, spinal pedicle screws connected to posterior rod assemblies to name just a couple examples. Other fixation devices are used to anchor suture to bone so the suture can be used to secure injured soft tissues.

Fixation devices typically have an elongate body, and one or more engaging feature(s) for retaining the device within body tissue or as part of a device assembly. The fixation device may either be inserted into body tissue directly, through a preformed hole with or without the aid of a tap, or as part of a device assembly within the bone cavity, such as with a screw/sheath assembly. Oftentimes fixation devices require the application of torsional forces from an insertion tool at one end of the implant to secure their application into body tissue, as with screw-type implants. Insertion tools are typically formed from an elongate shank having a mating feature formed on a distal end thereof for mating with a corresponding mating element formed on or in the head of the fixation device. One common type of driver tool includes a hexagonal-shaped or square-shaped socket for receiving a corresponding hexagonal-shaped or square-shaped head of a fixation device.

Certain conventional fixation devices and their drivers have some drawbacks. Device heads with hexagonal or square shaped cross-sections, for example, tend to have a relatively low stripping strength, meaning that under relatively small torque loads the drive head may be permanently damaged and torque transfer thus inhibited. If the head shape decreases the amount of material on the fixation device head or anchor head that interfaces with the driver, then the amount of material that needs to yield or be "stripped" from the drive head is reduced, thus reducing the stripping strength of the head.

Conventional fixation device heads also tend to have a relatively low failure torque, which can result in shearing of the head during insertion or stripping of the head elements necessary to transfer torque to the device. This type of failure can also be caused by the geometry of the head, which can reduce the overall cross-sectional area of the drive head. Fixation devices were historically constructed of implantable metals and alloys which afforded sufficiently high tensile and torsional strength to withstand the rigors of insertion, but the implant remained in the body for prolonged periods of time. Polymer, ceramic, or composite material systems, both biodegradable and non-biodegradable, have been developed for similar applications, but typically have lower tensile and torsional strength than metal counterparts, thus increasing the risk of device failure during application of high tortional torque loads during implantation in the body, as described above. More recently, biodegradable composite material systems have been developed that incorporate filler materials within the polymer matrix, such as calcium phosphate particles, which are osteoconductive. These filled systems may have further reduced tensile or torsional properties compared to unfilled polymer systems. Thus there is a need for an improved drive head for implantable fixation devices that has higher torsional resistance to strippage or shearing off.

One option to increase the failure torque of a fixation device is to increase the size of the head. Large device heads, however, require a large driver tool, which in turn requires a relatively large bone tunnel to be formed in the bone. This is particularly undesirable where the bone tunnel is to be formed in the cancellous bone, and where the procedure is minimally invasive and must traverse through a cannula or arthroscope. Accordingly, most fixation devices are adapted for use with a relatively small driver tool, and thus they have a relatively small drive head, which can result in a low failure torque and a low stripping strength, particularly in harder bone applications. A drive head of improved torsional strength is desirable to reduce the risk of deformation during insertion. Additionally, a drive head more resistant to deformation upon application of torsion may make a revision procedure easier, as there are some instances where torque driven devices need to be backed out and perhaps even reinserted.

Accordingly, there remains a need for fixation devices having improved physical properties, and in particular having a high failure torque and a high stripping strength.

SUMMARY OF THE INVENTION

The present invention provides a fixation device including an elongate shank that includes proximal and distal ends and defines a longitudinal axis. The shank further includes formed thereon at least one engaging member for facilitating placement of the device in body tissue, and securing the device in the tissue once implanted. The fixation device also includes a drive head having a proximal end, a distal end, and a radial cross-sectional geometry; where the distal end is mated to the proximal end of the elongate shank. The drive head includes at least one anti-rotational member having a longitudinal cross-sectional geometry integral with the drive head. The invention is also directed to fixation device installation kits containing the fixation device and a drive tool, as well as methods for attachment of tissue.

BRIEF DESCRIPTION OF THE DRAWINGS

The invention will be more fully understood from the following detailed description taken in conjunction with the accompanying drawings.

DETAILED DESCRIPTION OF THE INVENTION

The present invention provides a fixation device including an elongate shank defining a longitudinal axis and having at least one engaging member formed therewith to engage body tissue and facilitate placement of the device within the tissue and to secure the device in the tissue once implanted. The fixation device also includes a drive head for applying torsion to the elongate shank having a proximal end and a distal end and which is mated to the elongate shank so as to transfer the torsion to the elongate shank, thereby providing for placement of the device in tissue. The drive head may have a circular or a substantially non-circular radial cross-sectional geometry, for example oval, and includes at least one anti-rotational member (ARM) formed integrally therewith to provide for increased transfer of the torsion to the shank. In one embodiment the fixation device comprises a drive head of circular or substantially non-circular radial cross-sectional geometry with at least one ARM integral therewith. In a second embodiment, the fixation device comprises a drive head of circular or substantially non-circular radial cross-sectional geometry with multiple ARMs located on either side of a plane of symmetry for ease of inserter application. The ARMs are of configuration and dimension effective to provide a mating fit with the driver tool in order to ensure efficient transfer of torsion from the drive head to the shank. The presence of the ARMs provides high failure torque and high stripping strength.

In other aspects, a fixation device and installation kit is provided, including at least one fixation device and a cylindrical driver tool for cooperating with the fixation device. The fixation device has a shank with engaging member formed thereon and defining a longitudinal axis. A drive head is formed on the shank and has a circular or substantially non-circular radial cross-sectional geometry, such as oval, and at least one ARM formed integral therewith. The cylindrical driver tool has a distal end with a socket formed therein having a shape adapted to receive and engage the drive head of the fixation device. The ARM(s) also provide positive mating with the driver tool, such as a key in keyway configuration, to reduce driver slip-off, especially during off-angle insertions. In an exemplary embodiment, the driver tool has an outer diameter that is equal to or less than an outer-most diameter of the fixation device.

As shown in FIGS. 1A-1D, where like numbers refer to like features, the present invention generally provides a fixation device 10, including elongate shank 12 defining longitudinal axis A and having at least one engaging member 20 formed thereon. In the embodiment shown, engaging feature 20 is a helical thread. Drive head 30 has proximal end 32 and distal end 34 mated to elongate shank 12 at proximal end 14. In this case, drive head 30 has a substantially rectangular radial cross-sectional geometry, though drive head 30 could have substantially circular, rectangular, square, hexagonal, flattened oval or oval radial cross-sectional geometries, where the radial cross-section is defined as the cross-section perpendicular to longitudinal axis A.

The configuration of drive head 30 includes at least one ARM 36 protruding from and integral with drive head 30 and extending from distal end 34 to proximal end 32 of drive head 30. The configuration of drive head 30 with ARM 36 is particularly advantageous in that it provides fixation device 10 with improved physical properties, including high failure torque and high stripping strength.

Figure 1A:
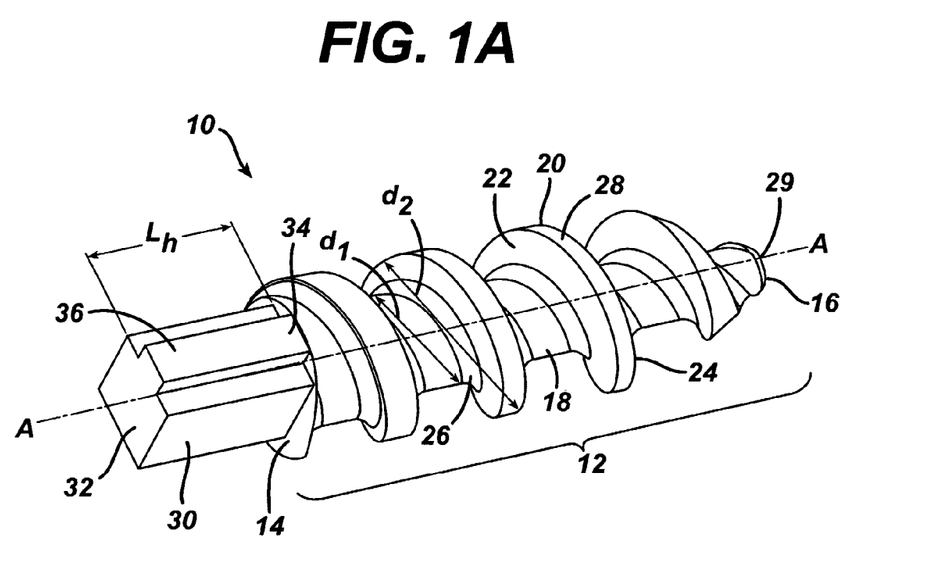
FIG. 1A is a perspective view of a fixation device of the present invention.
Figure 1B:
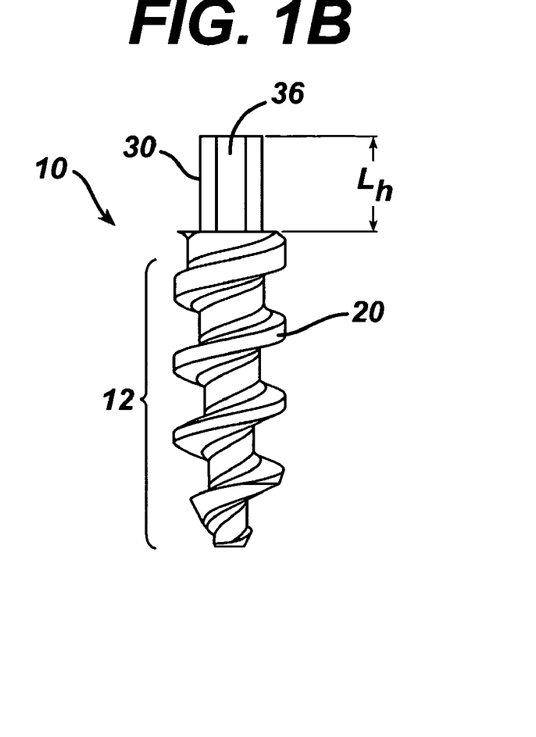
FIG. 1B is another perspective view of the fixation device shown in FIG. 1A.

Elongate shank 12 of fixation device 10 can have a variety of configurations and can include a variety of different engaging members 20 formed thereon. FIGS. 1A and 1B illustrate an exemplary embodiment of fixation device 10 having shank 12 including core 18 with single helical thread 20 extending around core 18 from proximal end 14 to distal end 16 of shank 12. Thread 20 includes proximal and distal facing flanks 22, 24 that extend between base 26 and substantially flattened crest 28. Thread 20 defines a major diameter $d_2$ of shank 12, which can vary along the length of shank 12, although major diameter $d_2$ is substantially constant along a substantial portion of shank 12. Threads 20, however, can taper at the distal portion of shank 12 to terminate at apex 29 of shank 12. Core 18 of shank 12 defines a minor diameter $d_1$ that can also be substantially constant or can vary along the length of shank 12. As shown in FIG. 1A, core 18 tapers from proximal end 14 to distal end 16. Once having the benefit of this disclosure, a person skilled in the art will appreciate that shank 12 shown in FIG. 1A is merely an exemplary embodiment of a shank 12, and that a variety of different shanks having different tissue-engaging members can be used with fixation device 10 in accordance with the present invention.

Figure 1C:
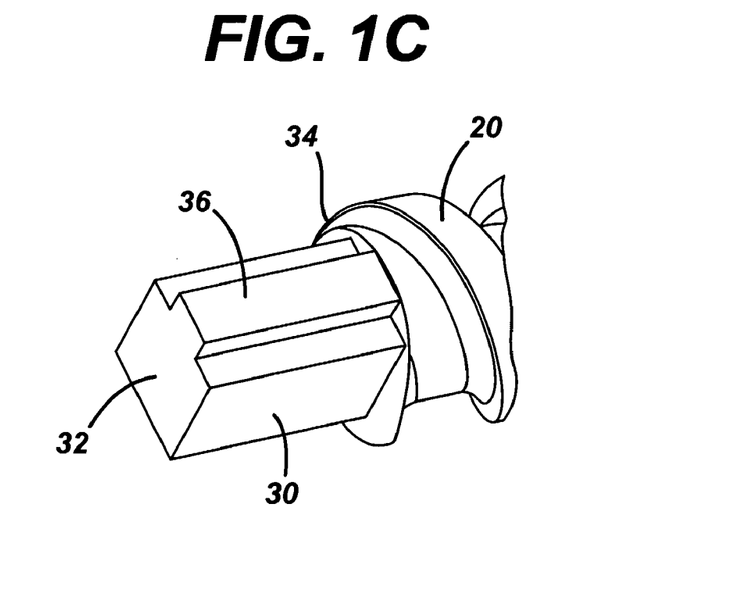
FIG. 1C is an enlarged, perspective view of the drive head portion of the fixation device shown in FIG. 1A.
Figure 1D:
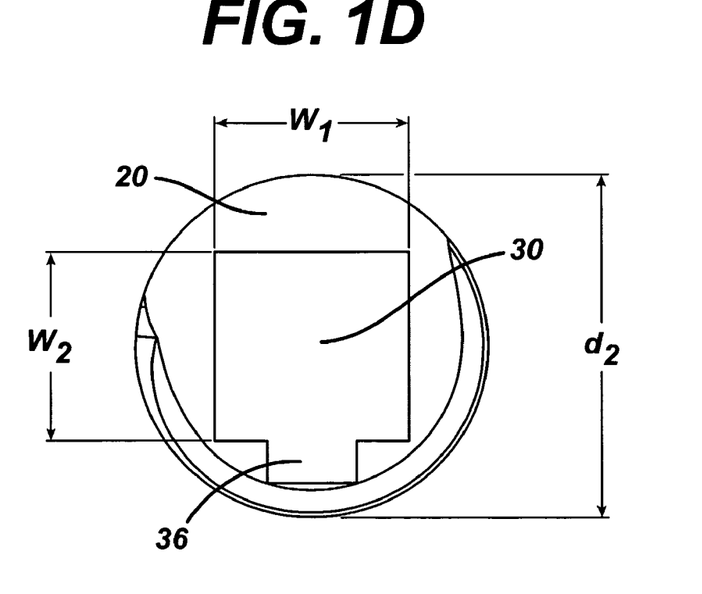
FIG. 1D is a top view of the fixation device shown in FIG. 1A.

Drive head 30 of fixation device 10 is shown in more detail in FIGS. 1C and 1D, and is attached to, or formed integrally with, shank 12. The relatively small size of widths $W_1$ and $W_2$ of drive head 30, as compared to major diameter $d_2$ of shank 12, is particularly desirable so that drive head 30 will not require a larger cavity to be formed in the tissue than necessary. Drive head 30 further includes length $L_h$ (shown in FIG. 1A) that extends between proximal and distal ends 32 and 34 thereof. Length $L_h$ of drive head 30 can vary, although length $L_h$ of drive head 30 may be optimized to allow the drive head to be received within a driver tool and to be driven into bone without shearing off. Drive head 30 has ARM 36 extending along length $L_h$ between distal end 34 and proximal end 32 of drive head 30.

Figure 2:
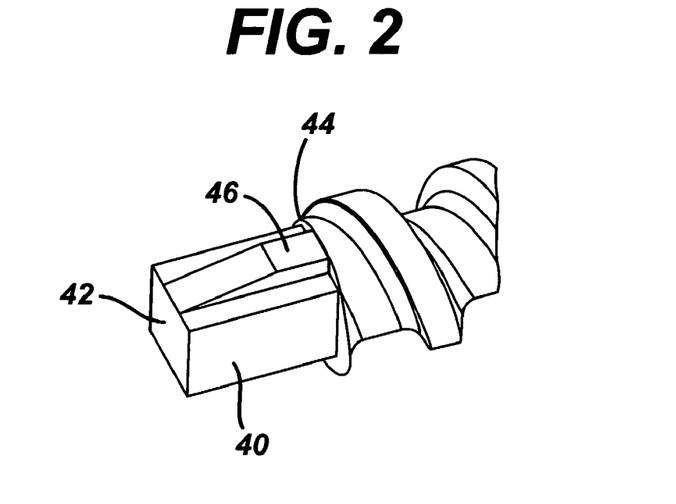
FIG. 2 is a perspective view of an alternate embodiment of the drive head portion of the present invention.

FIG. 2 shows an alternate embodiment of drive head 40 of a fixation device according to the present invention. In this embodiment, the radial cross-sectional geometry of drive head 40 is substantially square in shape with ARM 46 thereon that originates at distal end 44 and extends to proximal end 42. As shown, ARM 46 is tapered from proximal end 42 toward distal end 44. Once having the benefit of this disclosure, those skilled in the art will recognize that ARM 46 may be of other longitudinal cross-sectional geometries, e.g. parabolic, wedge, etc. without deviating from the scope of the invention, and that the ARM may extend only partially from distal end 44 toward proximal end 42 (not shown). Additionally, while not shown, ARM 46 may taper in the opposite orientation, i.e. from distal end 44 to proximal end 42.

Figure 3:
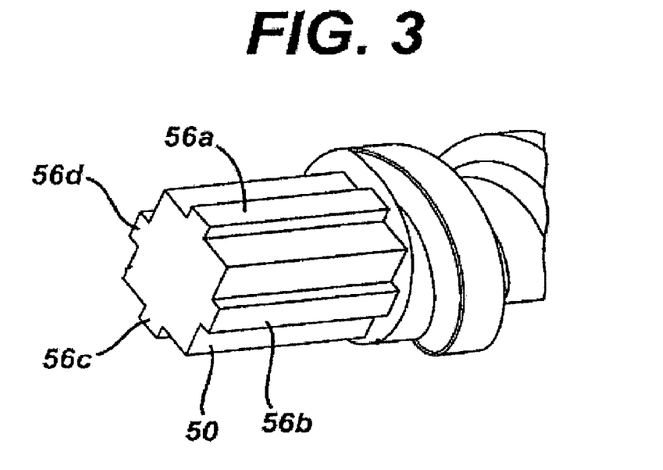
FIG. 3 is a perspective view of alternate embodiment of the drive head portion of the present invention.

FIG. 3 shows a further embodiment where drive head 50 contains four ARMs 56a, 56b, 56c and 56d positioned on opposing faces of drive head 50. A plurality of ARMs spaced equidistant around the drive head, such as depicted here, may be desirable from a procedural standpoint where the head possesses a plane of symmetry. In the embodiment depicted in FIG. 3, the radial cross-sectional geometry of drive head 50 is square, and thus has two planes of symmetry. With ARMs on either side of a plane of symmetry, rotational alignment of a mating inserter with respect to the implant is further alleviated. Multiple ARMs may also afford further improved physical properties. Once having the benefit of this disclosure, those skilled in the art will soon recognize other possible configurations with multiple ARMs on either side of a plane of symmetry keeping within the scope of the invention.

Figure 4:
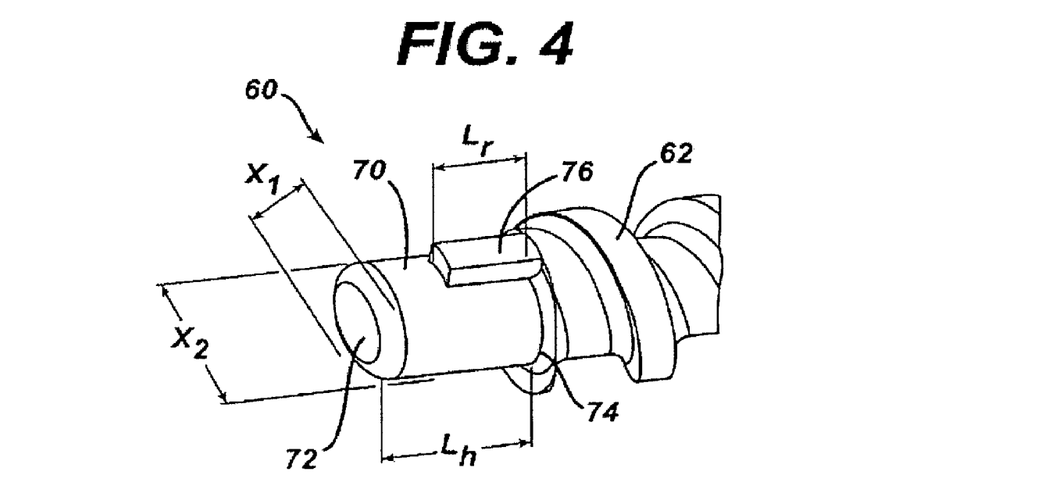
FIG. 4 is a perspective view of an alternate embodiment of the drive head portion of the present invention.

In FIG. 4, an alternate embodiment of drive head 70 is shown. Drive head 70 is substantially oval in radial cross-sectional shape defining a minor diameter $X_1$ and a major diameter $X_2$. Generally oval is known to include flattened ovals and ovals with flat portions perpendicular to the minor $X_1$ or major $X_2$ diameters of drive head 70. In an exemplary embodiment, minor diameter $X_1$ of head 70 is about three-fourths the size of major diameter $X_2$ of head 70, and major diameter $X_2$ of head 70 is equal to or less than minor diameter $d_1$ of shank 62. Drive head 70 contains ARM 76 integral therewith. ARM 76 originates at distal end 74 of driver head 70 and extends towards proximal end 72 for a total length of $L_r$. The length $L_r$ is less than or equal to the length $L_h$. Once having the benefit of this disclosure, those skilled in the art will soon recognize other possible configurations where the ARM may originate at proximal end 72 and extend towards distal end 74 for a length of $L_r$ (not shown).

Figure 5:
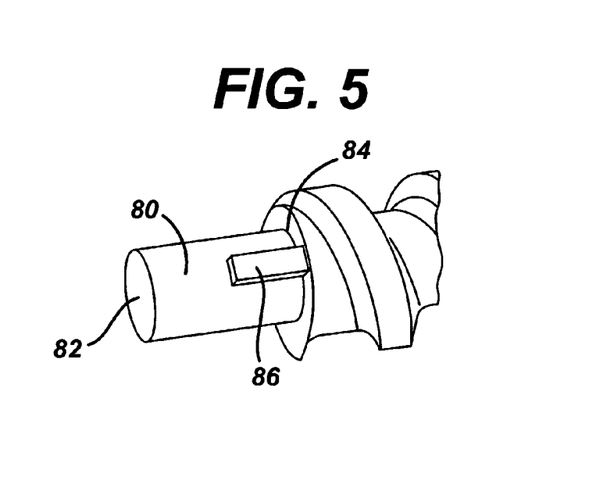
FIG. 5 is a perspective view of an alternate embodiment of the drive head portion of the present invention.

FIG. 5 shows another alternative embodiment of drive head 80. Drive head 80 is circular in radial cross-section and contains ARM 86 integral therewith. ARM 86 extends from distal end 84 towards proximal end 82.

Figure 6A:
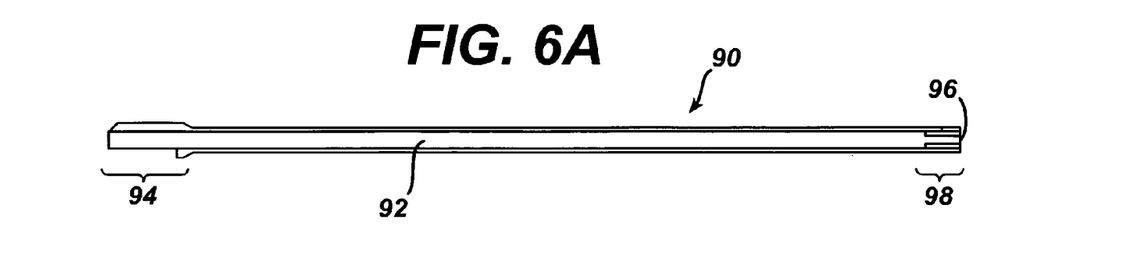
FIG. 6A is a side view of one embodiment of a driver tool in accordance with the present invention.
Figure 6B:
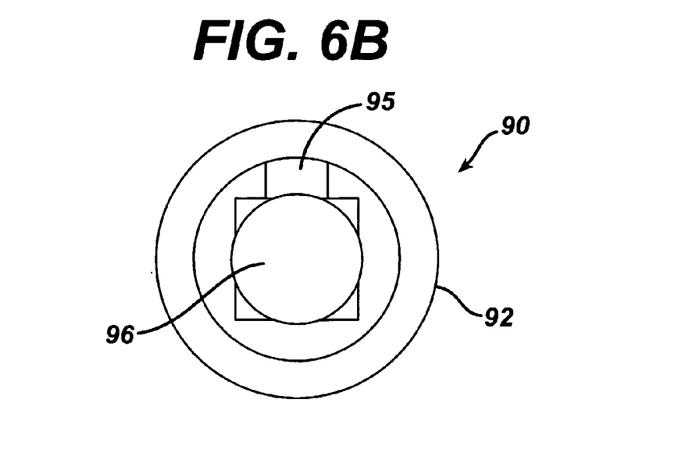
FIG. 6B is an end view of the distal-most end of the driver tool shown in FIG. 6A.
Figure 7A:
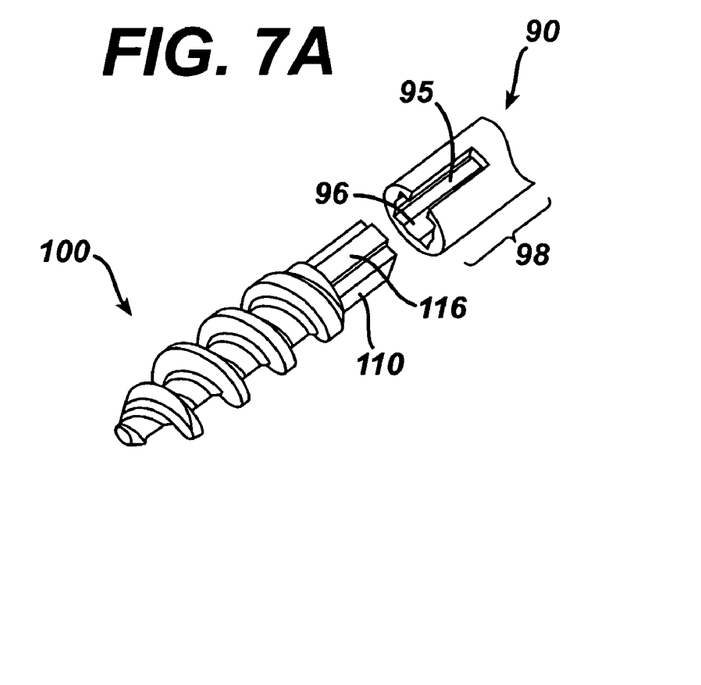
FIG. 7A is a perspective view of one embodiment of the fixation device and driver tool where the head of the device is not mated with the socket of the driver tool.
Figure 7B:
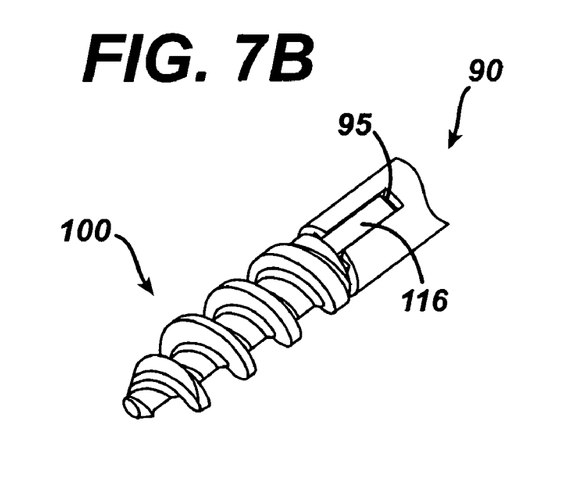
FIG. 7B is a perspective view of one embodiment of the fixation device and driver tool where the head of the device is mated with the socket of the driver tool.

For placement of fixation devices of the present invention into tissue, fixation devices can be driven into tissue using a driver tool, such as shown in FIGS. 6A-6B. Driver tool 90 can have a variety of shapes and sizes, but typically includes elongate shaft 92, having proximal handle portion 94 and distal end 98 having socket 96 formed therein and adapted to seat in mating relationship with the drive head of fixation devices of the present invention. As shown in FIGS. 7A-7B, socket 96 of driver tool 90 has an overall square shape and includes opposed ARM-engaging element 95 to engage and cooperate with ARM 116 once drive head 110 of fixation device 100 is placed in cooperation with socket 96 of drive tool 90. The shape of socket 96 and ARM-engaging elements 95 form a close fit with drive head 110 and cooperate with ARM 116 in such a way as to provide the mated relationship of drive head 110 within socket 96. The size and configuration of the socket 96 in relationship to drive head 110 and ARM 116 should be sufficient to provide a secure fit between drive head 110 and driver tool 90, and to prevent rotation of driver tool 90 with respect to fixation device 100. Driver tool 90 can also contain an inner lumen (not shown) extending there through for receiving free ends of suture.

Suitable materials from which fixation devices may be formed include biocompatible polymers selected from the group consisting of aliphatic polyesters, polyorthoesters, polyanhydrides, polycarbonates, polyurethanes, polyamides and polyalkylene oxides. The present invention also can be formed from biocompatible metals, glasses or ceramics, or from autograft, allograft, or xenograft bone tissues. Fixation devices can be further comprised of combinations of metals, ceramics, glasses and polymers.

The biocompatible materials can be biodegradable or non-biodegradable. Biodegradable materials, such as polymers, readily break down into small segments when exposed to moist body tissue. The segments then either are absorbed by the body, or passed by the body. More particularly, the biodegraded segments do not elicit permanent chronic foreign body reaction, because they are absorbed by the body or passed from the body, such that the body retains no permanent trace or residue of the segment.

In one embodiment, the device comprises biodegradable aliphatic polymer and copolymer polyesters and blends thereof. The aliphatic polyesters are typically synthesized in a ring opening polymerization. Suitable monomers include but are not limited to lactic acid, lactide (including L-, D-, meso and D,L mixtures), glycolic acid, glycolide, epsilon-caprolactone, p-dioxanone (1,4-dioxan-2-one), and trimethylene carbonate (1,3-dioxan-2-one).

In another embodiment, the materials comprising the devices will be biodegradable glasses or ceramics comprising mono-, di-, tri-, alpha-tri-, beta-tri-, and tetra-calcium phosphate, hydroxyapatite, calcium sulfates, calcium oxides, calcium carbonates, magnesium calcium phosphates, phospate glasses, bioglasses, and mixtures thereof.

In another embodiment, the materials comprising the devices can be combinations of biodegradable ceramics and polymers. Composites are prepared by incorporating biodegradable ceramic reinforcements such as fibers, short-fibers, or particles in a biodegradable polymer matrix.

Some particularly useful composites are 30 weight percent beta-tricalcium phosphate particles in 70 weight percent poly (lactic acid), or 30/70 beta-TCP/PLA, and 30 weight percent beta-tricalcium phosphate particles in 70 weight percent poly (lactide)/poly(glycolide) copolymer (mole ratio lactide to glycolyde 85/15), or 30/70 beta-TCP/(85/15 PLGA).

In another embodiment of the present invention, the polymers and blends can be used as a therapeutic agent release matrix. To form this matrix, the polymer would be mixed with a therapeutic agent prior to forming the device. The variety of different therapeutic agents that can be used in conjunction with the polymers of the present invention is vast. Therapeutic agents which may be administered via the pharmaceutical compositions of the invention include growth factors, including bone morphogenic proteins (i.e. BMP's 1-7), bone morphogenic-like proteins (i.e. GFD-5, GFD-7 and GFD-8), epidermal growth factor (EGF), fibroblast growth factor (i.e. FGF 1-9), platelet derived growth factor (PDGF), insulin like growth factor (IGF-I and IGF-II), transforming growth factors (i.e. TGF-beta I-III), vascular endothelial growth factor (VEGF); and other naturally derived or genetically engineered proteins, polysaccharides, glycoproteins, or lipoproteins.

Matrix materials for the present invention may be formulated by mixing one or more therapeutic agents with the polymer. Alternatively, a therapeutic agent could be coated on to the polymer, possibly with a pharmaceutically acceptable carrier. Any pharmaceutical carrier can be used that does not dissolve the polymer. The therapeutic agent may be present as a liquid, a finely divided solid, or any other appropriate physical form. Typically, but optionally, the matrix will include one or more additives, such as diluents, carriers, excipients, stabilizers or the like.

Methods for using a fixation device in accordance with the present invention are also provided. The medical fixation device is attached to a driver tool, the neighboring tissue segments are approximated, the medical fixation device is inserted into the approximated neighboring tissue segments, and the driver tool is removed.

The fixation devices disclosed herein may be used in different ways to assist in the reconstruction of damaged body tissue. They may be used to directly secure tissue in close approximation to neighboring tissue to effect healing. They may provide mechanical stability and load sharing during the healing process, as when a graft is secured in a bone tunnel for ACL reconstruction. Fixation devices of the present invention may also be used in conjunction with other device hardware such as plates, rods, or various other connecting members known in the art as part of an implant assembly.

What is claimed is:

1. A medical fixation device installation kit, comprising:
   at least one medical fixation device having an elongate shank comprising a proximal end and a distal end and defining a longitudinal axis and comprising at least one engaging member formed thereon; and a solid drive head comprising a proximal end, a distal end mated to said elongate shank, a radial cross-sectional geometry, and at least one anti-rotational member comprising a longitudinal cross-sectional geometry integral with said drive head; and
   a cylindrical driver tool having a distal end comprising a socket formed therein having a cutout extending through a sidewall of the driver tool and adapted to receive and engage said anti-rotational member of said drive head of said medical fixation device such that the driver tool is prevented from rotating in any direction relative to the drive head,
   wherein said drive head has a maximum width that is not greater than a major diameter of the elongate shank.

2. The medical fixation device installation kit of claim 1 wherein said elongate shank tapers from said proximal end to said distal end.

3. The medical fixation device installation kit of claim 1 wherein said at least one engaging member comprises a helical thread.

4. The medical fixation device installation kit of claim 1 wherein said radial cross-sectional geometry of said drive head is non-circular.

5. The medical fixation device installation kit of claim 4 wherein said radial cross-sectional geometry of said drive head is rectangular, square, hexagonal, flattened oval or oval.

6. The medical fixation device installation kit of claim 5 wherein said radial cross-sectional geometry of said drive head is oval.

7. The medical fixation device installation kit of claim 1 wherein said anti-rotational member extends proximally along the length of the drive head.

8. The medical fixation device installation kit of claim 1 wherein said anti-rotational member is tapered proximally along the length of said drive head.

9. The medical fixation device installation kit of claim 1 wherein an even number of said anti-rotational members are symmetrically disposed on said drive head about a plane of symmetry of said drive head.

10. The medical fixation device installation kit of claim 1 wherein said longitudinal cross-sectional geometry of said anti-rotational member is rectangular, curved, parabolic, or triangular.

11. The medical fixation device installation kit of claim 1 wherein said device comprises a biodegradable material.

12. The medical fixation device installation kit of claim 11 wherein said biodegradable material is a polymer, copolymer, or polymer blend formed from monomers selected from the group consisting of lactic acid, lactide, glycolic acid, glycolide, epsilon-caprolactone, 1,4-dioxan-2-one and 1,3-dioxan-2-one.

13. The medical fixation device installation kit of claim 11 wherein said biodegradable material is selected from the group consisting of biodegradable glass, mono-calcium phosphate, dicalcium phosphate, tricalcium phosphate, alpha-tricalcium phosphate, beta-tricalcium phosphate, tetracalcium phosphate, hydroxyapatite, calcium sulfate, calcium oxide, calcium carbonate, magnesium calcium phosphate, phosphate glass and bioglass.

14. The medical fixation device installation kit of claim 11 wherein said biodegradable material is a composite comprised of beta-tricalcium phosphate and poly(lactide).

15. The medical fixation device installation kit of claim 11 wherein said biodegradable material is a composite comprised of 30 weight percent beta-tricalcium phosphate particles in 70 weight percent poly(lactide)/poly(glycolide) copolymer, wherein the mole ratio of lactide to glycolyde is 85/15.

16. The medical fixation device installation kit of claim 1 wherein the socket and the cutout have a shape that corresponds to a shape of the drive head and the anti-rotational member.

17. The medical fixation device installation kit of claim 1 wherein said distal end of said drive head is coupled to said proximal end of said elongate shank, and wherein said anti-rotational member longitudinally extends from said distal end of said drive head to said proximal end of said drive head.

18. The medical fixation device installation kit of claim 1 wherein said anti-rotational member extends along less than a longitudinal length of said drive head between said proximal and distal ends of said drive head.

* * * * *